United States Patent [19]

Nakajima et al.

[11] Patent Number: 5,064,644
[45] Date of Patent: Nov. 12, 1991

[54] WATER-IN-OIL EMULSION TYPE COSMETIC COMPOSITION

[75] Inventors: Hideo Nakajima; Kiyoshi Kawada; Kazuo Tokubo, all of Yokohama, Japan

[73] Assignee: Shiseido Company Ltd., Tokyo, Japan

[21] Appl. No.: 588,520

[22] Filed: Sep. 24, 1990

Related U.S. Application Data

[63] Continuation of Ser. No. 321,599, Mar. 10, 1989, abandoned, which is a continuation of Ser. No. 138,242, Dec. 24, 1987, abandoned, which is a continuation of Ser. No. 769,641, Aug. 26, 1985, abandoned.

[30] Foreign Application Priority Data

Aug. 27, 1984 [JP]  Japan ................................. 59-178060

[51] Int. Cl.$^5$ ................... A61K 31/745; A61K 7/021; A61K 31/74
[52] U.S. Cl. ........................ 424/83; 424/63; 424/78; 514/844; 514/845; 514/937
[58] Field of Search ............... 424/63, 78, 83; 514/844, 845, 937

[56] References Cited

U.S. PATENT DOCUMENTS 3,489,690  1/1970  Lachampt et al. ............... 252/308
4,171,455 10/1979  Tomita et al. ................... 568/625
4,486,405 12/1984  Klein ................................ 424/59

OTHER PUBLICATIONS

Zuckerman, Cosmetic Science and Technology, vol. 3, 1974, pp. 560–561.

*Primary Examiner*—John W. Rollins
*Attorney, Agent, or Firm*—Sprung Horn Kramer & Woods

[57] ABSTRACT

A water-in-oil emulsion type cosmetic composition comprising 0.1% to 20% by weight of a propylene oxide-ethylene oxide addition product having the general formula (I):

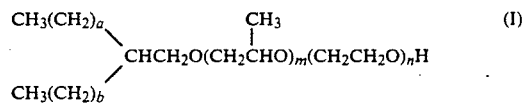

wherein a is an integer of 7 to 19, b is an integer of a+2, m is an average addition mol number of 5 to 30, and n is an average addition mol number of 5 to 30, and 0.01% to 20% by weight of an iron oxide.

This water-in-oil emulsion type cosmetic composition has excellent emulsification stability and excellent dispersion stabililty of an iron oxide pigment at a wide temperature range.

6 Claims, No Drawings

WATER-IN-OIL EMULSION TYPE COSMETIC COMPOSITION

This application is a continuation of application Ser. No. 321,599, filed 3/10/89, now abandoned, which is a continuation of application Ser. No. 138,242, filed 12/24/87, now abandoned, which is a continuation of application Ser. No. 769,641, filed 8/26/85, now abandoned.

BACKGROUND OF THE INVENTION

1. Field of the Invention

The present invention relates to a novel water-in-oil (i.e., "W/O") emulsion type cosmetic composition. More specifically, it relates to a W/O emulsion type cosmetic composition having an excellent emulsification stability and excellent dispersion stability of an iron oxide pigment at a wide temperature range.

2. Description of the Related Art

In the production of W/O emulsion type cosmetics, lipophilic emulsifiers having a relatively low hydrophilic-lipophilic balance (i.e., "HLB") such as sorbitan fatty acid partial esters, polyoxyethylene (i.e., "POE") sorbitan fatty acid partial esters, glycerol fatty acid partial esters, diglycerol fatty acid partial esters, POE sorbitol fatty acid partial esters, POE alkyl ethers, and castor oil POE addition products are generally used as an emulsifier. These W/O emulsion type compositions have a relatively good stability at an ambient temperature when nonpolar oil such as paraffin oil is contained. However, in the case of nonpolar oil, the oil phase is easily separated at an elevated temperature. Furthermore, when polar oils such as triglycerides, which are selium analogues components, and waxes are contained, the W/O emulsion type compositions are inverted to an oil-in-water (i.e., O/W) emulsion or water separation from the emulsion occurs even at room temperature. Thus, the formation of stable W/O emulsion type compositions is difficult in the art. Especially when iron oxides conventionally used in the make-up type cosmetics are intended to be formulated into the above-mentioned W/O emulsion type cosmetic compositions, it is difficult to ensure the dispersion stability of the iron oxides, in addition to the above-mentioned emulsification stability. Iron oxides pigments are said to be substantially essential in make-up cosmetic compositions. Furthermore, W/O emulsion type cosmetic compositions containing an iron oxide does not flow during, for example, perspiration and, therefore, the make-up stays long. Consequently, the preparation of stable W/O emulsion type cosmetic compositions containing an iron oxide pigment is strongly desired in the art. Various attempts have been made to improve the stability of W/O emulsion type cosmetic compositions containing an iron oxide. For example, the use of various coemulsifiers such as polyols, amino acids and the salts thereof, pyrrolidone carboxylic acid salts, and metallic soaps are proposed in, for example, Japanese Examined Patent Publication No. 48-15798 and Japanese Unexamined Patent Publication No. 55-31037. However, satisfactory W/O emulsion type cosmetic compositions containing an iron oxide have not been developed yet.

SUMMARY OF THE INVENTION

Accordingly, the objects of the present invention are to eliminate the above-mentioned disadvantages in conventional W/O emulsion type cosmetic compositions and to provide a W/O emulsion type cosmetic composition having an excellent emulsification stability and excellent dispersion stability of an iron oxide pigment at a wide temperature range.

Other objects and advantages of the present invention will be apparent from the description set forth hereinbelow.

In accordance with the present invention, there is provided a water-in-oil emulsion type cosmetic composition comprising 0.1% to 20% weight of a propylene oxide-ethylene oxide addition product having the general formula (I):

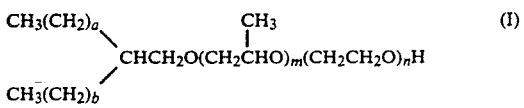

wherein a is an integer of 7 to 19, b is an integer of a+2, m is an average addition mol number of 5 to 30, and n is an average addition mol number of 5 to 30, and 0.01% to 20% by weight of an iron oxide.

DESCRIPTION OF THE PREFERRED EMBODIMENTS

The propylene oxide-ethylene oxide addition products having the general formula (I) used in the present invention are those having a branched alcohol mother nucleus with a carbon number (a+b+2) of 18 to 40, preferably 20 to 36. The use of the propylene oxide-ethylene oxide addition products having a total carbon number (a+b+2) of less than 18 does not satisfactorily improve the stability of the resultant compositions. The "m" in the general formula (I) represents an average mol number of propylene oxide added per one mol of the above-mentioned alcohol having a branched alkyl group. The "n" in the general formula (I) represents an average mol number of ethylene oxide added per one mol of the alcohol. The use of the addition product having an average propylene oxide addition mol number m of 4 or less does not provide the desired effect obtained by the addition of propylene oxide. The average addition mol number of the propylene oxide in the addition product (I) is 5 to 30, preferably 10 to 30. The "n" in the addition product having the general formula (I) is generally 5 to 30, preferably 8 to 20, which is larger than that of conventional ethylene oxide addition type W/O emulsifiers (i.e., n=1 to 5). The conventional emulsifier having ethylene oxide addition mol number of 5 to 30 usually form an O/W emulsion and, therefore, a W/O emulsion type composition cannot be formed or only a very unstable W/O emulsion type composition can be obtained, even if possible. Especially when an iron oxide pigment is further incorporated into the composition, the stability becomes worse. Contrary to this, it is believed that, since the propylene oxide-ethylene oxide addition product used in the present invention has the propylene oxide chain and the branched alkyl group, an iron oxide-containing W/O emulsion type cosmetic composition having excellent stability can be obtained according to the present invention.

Typical examples of propylene oxide-ethylene oxide addition products usable in the present invention are polyoxyethylene (15) polyoxypropylene (8)-2-tetradecyloctadecyl ether, polyoxyethylene (10) polyoxypropylene (20)-2-decyl-tetradecyl ether, polyoxyethylene (8) polyoxypropylene (15)-2-octyl-dodecyl ether, polyoxyethylene (10) polyoxypropylene (30)-2-heptylundecyl ether, polyoxyethylene (30) polyethylene (25)-2-octadecyl-docosyl ether, polyoxyethylene (25) polyethylene (10)-2-hexadecyl-eicosyl ether. These propylene oxide-ethylene oxide addition products may be used alone or in any mixture thereof.

The propylene oxide-ethylene oxide addition product is generally formulated into the W/O emulsion type cosmetic composition according to the present invention in an amount of 0.1% to 20% by weight, preferably 0.5% to 5% by weight, based on the total weight of the composition. The amount of the addition product of less than 0.1% by weight will not stabilize the W/O emulsion type cosmetic composition. The use of too large an amount of the addition product results in no substantial increase in stability of the cosmetic composition. Thus, the maximum amount of the propylene oxide-ethylene oxide addition product is 20% by weight.

The iron oxides usable in the present invention include, for example, iron oxide (yellow), iron oxide (red) (i.e., red oxide or rouge), and iron oxide (black). These iron oxides may be used alone or in any mixture thereof. Furthermore, other conventional pigments may be used, in addition to the above-mentioned iron oxide pigment, in the present invention.

The iron oxide is generally formulated into the W/O emulsion type cosmetic composition in an amount of 0.01% to 20% by weight, preferably 0.05% to 10% by weight, based on the total amount of the W/O emulsion type cosmetic composition. The use of too small an amount of the iron oxide cannot provide a desirable coloration of the cosmetic composition, whereas the use of too large an amount of the iron oxide will adversely affect the emulsification stability of the W/O emulsion type cosmetic composition.

The W/O emulsion type cosmetic compositions according to the present invention further contain 5% to 98% by weight, preferably 15% to 97% by weight, of oil based on the total weight of the cosmetic composition. Examples of the oil usable in the present invention are hydrocarbons such as paraffin oil, squalane, paraffin wax, and ceresin; natural animal and vegetable oils, fats, and waxes such as olive oil, camellia oil, soybean oil, Macademia nut oil, castor oil, lanoline, carnauba wax, candelilla wax, whale wax, beeswax, and jojoba oil; fatty acids having 10 to 35 carbon atoms; alcohols having 10 to 35 carbon atoms; synthetic esters having 16 or more carbon atoms such as isopropyl myristate, glycerol di-isostearate, grycerol tri-2-ethylhexanate, diisostearyl malate, and myristyl myristate. These oils may be used alone or in any mixture thereof. The formulating ratio of the oil to water in the W/O emulsion type cosmetic composition is 5:95 to 99:1 (by weight), preferably 15:85 to 97:3.

The W/O emulsion type cosmetic compositions according to the present invention may optionally contain, in addition to the above mentioned essential constituents, other conventional ingredients used in cosmetic compositions. Examples of such conventional ingredients are other surfactants, humectants, dyes, pigments, UV absorbers, perfumes, pharmaceutically active agents, preservatives, and anti-oxidants.

The W/O emulsion type cosmetic compositions according to the present invention have excellent storage stability (i.e., emulsification stability and dispersion stability) at a wide temperature range when compared to conventional W/O emulsion type cosmetic compositions. Especially, according to the present invention, iron oxides, which are desired but are not formulated into W/O emulsion type cosmetic compositions, can be stably formulated and, therefore, the present invention is practically useful in the cosmetic fields, especially the make-up cosmetic field.

EXAMPLE

The present invention will be further explained by, but is by no means limited to, the following Examples and Comparative Examples. Parts in the formulation amounts of the Examples and Comparative Examples are by weight unless otherwise specified.

EXAMPLES 1 TO 10 AND COMPARATIVE EXAMPLES 1 TO 10

A 42 part amount of an oil listed in Table 1, 3 parts of an emulsifier listed in Table 1, 3 parts of iron oxide (red), and 50 parts of water were heated to a temperature of 70° C. and were mixed and emulsified, while stirring, to prepare W/O emulsion type compositions. After preparation, the type of emulsion was confirmed as a W/O type in each case by electric conductivity.

The stability of the resultant compositions was evaluated as follows.

Namely, the composition was allowed to stand at a temperature of 70° C. for 1 day (in atmospheric environment) and the condition was observed. The emulsification stability was evaluated by the separated volumes of the oil and aqueous phases and the dispersion stability of the iron oxide was evaluated by the settling amount of the iron oxide in the composition.

The evaluation standards of the emulsification stability and dispersion stability were as follows.

EMULSIFICATION STABILITY

⊚ . . . No separation
○ . . . Slight oil phase separation
△ . . . Oil phase separation and slight aqueous phase separation
x . . . Separation into cream, oil, and aqueous phases
xx . . . Separation into oil and aqueous phases

DISPERSION STABILITY

○ . . . Substantially no settling
△ . . . Settling of less than half of volume
x . . . Settling of more than half of volume In the comparative Examples, conventional W/O emulsion type emulsifiers were used.

The results are as shown in Tables 1 and 2.

TABLE 1

| Example No. | Numbers of a, b, m, and n in the general formula (I) | | Oil | Type of emulsion type | Emulsification stability | Dispersion stability |
|---|---|---|---|---|---|---|
| 1 | a = 10  m = 20 | b = 12  n = 10 | Paraffin oil | W/O | ⊚ | ○ |
| 2 | a = 10  m = 20 | b = 12  n = 10 | Olive oil | W/O | ⊚ | ○ |

TABLE 1-continued

| Example No. | Numbers of a, b, m, and n in the general formula (I) | | Oil | Type of emulsion type | Emulsification stability | Dispersion stability |
|---|---|---|---|---|---|---|
| 3 | a = 10 m = 30 | b = 12 n = 12 | Isopropyl myristate | W/O | ⊙ | o |
| 4 | a = 10 m = 10 | b = 12 n = 8 | Jojoba oil | W/O | ⊙ | o |
| 5 | a = 7 m = 5 | b = 9 n = 5 | Candelilla wax | W/O | o | o |
| 6 | a = 8 m = 25 | b = 10 n = 12 | Glycerol triisostearate | W/O | ⊙ | o |
| 7 | a = 12 m = 15 | b = 14 n = 15 | Japan wax | W/O | ⊙ | o |
| 8 | a = 14 m = 25 | b = 16 n = 20 | Glycerol tri-2-ethylhexanate | W/O | ⊙ | o |
| 9 | a = 16 m = 20 | b = 18 n = 30 | Castor oil | W/O | ⊙ | o |
| 10 | a = 19 m = 8 | b = 21 n = 10 | Diisostearyl malate | W/O | ⊙ | o |

TABLE 2

| Comparative Example No. | Emulsifier | Oil | Type of emulsion | Emulsification stability | Dispersion stability |
|---|---|---|---|---|---|
| 1 | POE (4) Oleylether | Olive oil | W/O | x | — |
| 2 | Sorbitan sesquioleate | " | W/O | x | — |
| 3 | POE (3) sorbitan monooleate | " | O/W | x | — |
| 4 | Glycerol monooleate | " | O/W | x | — |
| 5 | Glycerol monooleate + 70% aqueous sorbitol (1:9) | " | W/O | x | — |
| 6 | Diglycerol diisostearate | Castor oil | W/O | xx | — |
| 7 | POE (5) POP (8) cetyl ether | " | W/O | xx | — |
| 8 | POE (60) hydrogenated castor oil | " | W/O | o | x |
| 9 | POE (30) hydrogenated castor oil | " | W/O | o | x |
| 10 | Diglycerol dioleate + Diglycerol (1:5) | " | W/O | xx | — |

POE: Polyoxyethylene group
POP: Polyoxypropylene group

As shown in Tables 1 and 2, the W/O emulsion type compositions of Examples 1 to 10 emulsified and dispersed by using the ethylene oxide-propylene oxide addition products according to the present invention were stable. Contrary to this, most of the W/O emulsion type compositions of the Comparative Examples had poor emulsification stability and no composition having a good dispersion stability was obtained in the Comparative Examples.

In the cases where yellow and black iron oxides were used in the compositions according to the Examples, similar results were obtained.

EXAMPLE 11

PREPARATION OF EMULSION TYPE LIPSTICK (Formulation)

| Ingredient | Part |
|---|---|
| (1) Castor oil | 50 |
| (2) Glycerol diisosteate | 10 |
| (3) Candelilla wax | 8 |
| (4) Solid paraffin | 10 |
| (5) POE (20) POP (20)-2-tetradecyl-octadecyl ether | 4 |
| (6) D & C Red No. 7 | 1 |
| (7) D & C Red No. 30 | 0.5 |
| (8) Titanium oxide | 1 |
| (9) Iron oxide (red) | 1.5 |
| (10) Iron oxide (yellow) | 1 |
| (11) Purified water | 10 |
| (12) Glycerol | 3 |

(Preparation)

The ingredients (1) to (5) were uniformly dissolved at a temperature of 80° C. while agitating. The ingredients (6) to (10) were added and dispersed therein. Furthermore, the ingredients (11) and (12) were added and the mixture was emulsified. While the agitation was continued, the emulsion was packed into a molded container and was cooled. Thus, the desired lipstick was obtained.

COMPARATIVE EXAMPLE 11

The lipstick was prepared in the same manner as in Example 11, except that 0.4 parts of glycerol monooleate and 3.6 parts of a 70% aqueous sorbitol solution were used in lieu of the POE(20) POP(20)-2-tetradecyloctadecyl ether.

COMPARATIVE EXAMPLE 12

The lipstick was prepared in the same manner as in Example 11, except that POE(40) hydrogenated castor oil was used in lieu of the POE(20) POP(20)-2-tetradecyloctadecyl ether.

The lipstick prepared in Comparative Example 11 caused the water separation immediately after emulsification. In comparative Example 12, although the emulsification was effected, the iron oxide was aggregated and did not exhibit the inherent color tone and, although the agitation was continued for further one hour, aggregation of the iron oxide was further caused and all of the iron oxide was finally settled.

Contrary to the above, the W/O emulsion type composition having excellent emulsification stability and dispersion stability was obtained in Example 11.

In order to evaluate the dispersion conditions of the iron oxide, the change ($\Delta E$) in the color tone of the compositions of Examples 11 and Comparative Example 12 were determined 10 minutes and 1 hour after the preparation, while the agitation was continued immediately after the preparation, by using a color analyzer manufactured by Hitachi Ltd. The results are as shown in Table 3.

TABLE 3

|  | Agitation time | Example 11 | Comparative Example 12 |
|---|---|---|---|
| $\Delta E$ | 10 min | 0.29 | 5.35 |
|  | 1 hr | 0.37 | Settled out |

As is clear from the results shown in Table 3, the iron oxide in Example 11 was excellently dispersed, whereas the iron oxide in Comparative Example 12 was aggregated.

The cosmetic composition in Example 11 was stable after the composition was allowed to stand at temperatures of 37° C., room temperature, and 0° C., for 3 months or more.

EXAMPLE 12

PREPARATION OF CREAM FOUNDATION (Formulation)

| Ingredient | Part |
|---|---|
| (1) Isopropyl myristate | 17 |
| (2) Squalane | 10 |
| (3) Lanolin | 7 |
| (4) Microcrystalline wax | 3 |
| (5) POE (8) POP (15)-2-decyltetradecyl ether | 3 |
| (6) Butyl p-hydroxybenzoate | 0.1 |
| (7) Kaolin | 5 |
| (8) Talc | 10 |
| (9) Titanium oxide | 2 |
| (10) Iron oxide (red) | 0.2 |
| (11) Iron oxide (yellow) | 0.8 |
| (12) Perfume | 0.1 |
| (13) Purified water | 36.7 |
| (14) Propylene glycol | 5 |
| (15) Methyl p-hydroxybenzoate | 0.1 |

(Preparation)

The ingredients (1) to (6) were uniformly dissolved at a temperature of 70° C. and the ingredients (7) to (11) were then added and dispersed therein. The ingredients (13) and (15) were further added and the mixture was emulsified. While the agitation was continued, the emulsion was cooled to obtain the desired W/O cream foundation.

The cream foundation thus obtained was stable and had an excellent dispersion stability of the iron oxide during the preparation. Furthermore, after the compositions were allowed to stand at 0° C., room temperature, and 37° C. for 3 months, no separation of the oil and water occurred and the emulsion was stable.

The resultant foundation had an excellent creamy application feeling and kept the make-up fresh.

EXAMPLE 13

PREPARATION OF W/O TYPE STICK FOUNDATION (Formulation)

| Ingredient | Part |
|---|---|
| (1) Macadamia nut oil | 25 |
| (2) Vaseline | 5 |
| (3) Ceresin | 5 |
| (4) POE (10) POP (15)-2-dodecylhexadecyl ether | 4 |
| (5) Kaolin | 15 |
| (6) Mica | 20 |
| (7) Titanium oxide | 8 |
| (8) Iron oxide (red) | 1 |
| (9) Iron oxide (yellow) | 3 |
| (10) Methyl p-hydroxybenzoate | 0.1 |
| (11) Perfume | 0.1 |
| (12) Purified water | 10.8 |
| (13) Dipropylene glycol | 3 |

(Preparation)

The ingredients (1) to (4) were uniformly dissolved at a temperature of 80° C. and the ingredients (5) to (10) were added and dispersed therein. The ingredients (12) and (13) were further added and the mixture was emulsified. While the agitation was continued, the ingredient (11) was added, and then the emulsion was cast into a container. The emulsion was cooled to obtain the desired W/O type solid foundation.

EXAMPLE 14

PREPARATION OF W/O EMULSION TYPE ROUGE (Formulation)

| Ingredient | Part |
|---|---|
| (1) Glycerol tri-2-ethylhexanate | 20 |
| (2) Hydrogenated lanolin | 15 |
| (3) Microcrystalline wax | 5 |
| (4) POE (15) POP (30)-2-octyldodecyl ether | 3 |
| (5) Talc | 20 |
| (6) Titanium oxide | 5 |
| (7) Iron oxide (red) | 3 |
| (8) Iron oxide (yellow) | 1 |
| (9) Iron oxide (black) | 0.1 |
| (10) D & C Red No. 6 | 1 |
| (11) Butyl p-hydroxybenzoate | 0.1 |
| (12) Perfume | 0.1 |
| (13) Purified water | 21.7 |
| (14) Glycerol | 5 |

(Preparation)

The ingredients (1) to (4) were uniformly dissolved at a temperature of 80° C. and the ingredients (5) to (10) were then dispersed therein. The ingredients (13) and (14) were further added and the mixture was emulsified. While the agitation was continued, the ingredient 12 was added. The resultant emulsion was cast into a container. After cooling, the desired W/O emulsion type rouge was obtained.

The stick foundation of Example 13 and the W/O emulsion type rouge of Example 14 were stable when they were stored for a long period of time. The resultant stick foundation and rouge had excellent creamy application feeling and kept the make-up fresh.

We claim:

1. A water-in-oil emulsion type cosmetic composition comprising (i) 0.1% to 20% by weight of a propylene oxide-ethylene oxide addition product having the general formula (I):

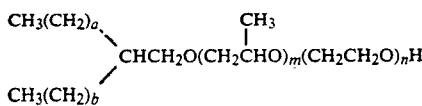

wherein a is an integer of 7 to 19, b is an integer of a+2, m is an average addition mol number of 5 to 30, and n is an average addition mol number of 5 to 30, (ii) 0.01% to 20% by weight of an iron oxide, (iii) 15% to 97% by weight of oil, and (iv) water in a weight ratio of the oil to water of 15:85 to 97:3.

2. A cosmetic composition as claimed in claim 1, wherein said propylene oxide-ethylene oxide addition product is at least one member selected from the group consisting of polyoxyethylene (15) polyoxypropylene (8)-2-tetradecyl-octadecyl ether, polyoxyethylene (10) polyoxypropylene (20)-2-decyl-tetradecyl ether, polyoxyethylene (8) polyoxypropylene (15)-2-octyldodecyl ether, polyoxyethylene (10) polyoxypropylene (30)-2-heptyl-undecyl ether, polyoxyethylene (30) polyethylene (25)-2-octadecyl-docosyl ether, polyoxyethylene (25) polyethylene (10)-2-hexadecyl-eicosyl ether.

3. A cosmetic composition as claimed in claim 1, wherein said iron oxide is at least one member selected from the group consisting of iron oxide (yellow), iron oxide (red), and iron oxide (black).

4. A cosmetic composition as claimed in claim 1, wherein said iron oxide is present in about 0.05 to 10% by weight.

5. A cosmetic composition as claimed in claim 1, wherein (i) and (ii) each is present in about 3 parts by weight, (iii) is present in about 41 to 50 parts by weight, and (iv) is present in about 50 parts by weight.

6. A method of stabilizing a water-in-oil emulsion containing 0.01 to 20% by weight of an iron oxide which comprises adding thereto 0.1 to 20% by weight of a propylene oxide-ethylene oxide addition product having the general formula (I):

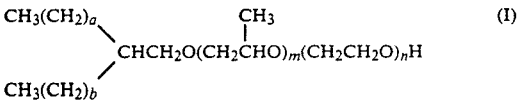

wherein a is an integer of 7 to 19, b is an integer of a+2, m is an average addition mol number of 5 to 30, and n is an average addition mol number of 5 to 30.

* * * * *